United States Patent
Burkatovsky

(10) Patent No.: US 6,825,484 B2
(45) Date of Patent: Nov. 30, 2004

(54) SURFACE REFLECTIVITY DISCRIMINATING DEVICE

(75) Inventor: Vitaly Burkatovsky, Rishon LeZion (IL)

(73) Assignee: Creo IL. Ltd., Herzlia Pituah (IL)

( * ) Notice: Subject to any disclaimer, the term of this patent is extended or adjusted under 35 U.S.C. 154(b) by 198 days.

(21) Appl. No.: 10/315,005

(22) Filed: Dec. 10, 2002

(65) Prior Publication Data

US 2004/0057053 A1 Mar. 25, 2004

Related U.S. Application Data

(63) Continuation-in-part of application No. 10/252,039, filed on Sep. 23, 2002.

(51) Int. Cl.$^7$ ................................................. G01N 21/86
(52) U.S. Cl. ........................... 250/559.18; 250/559.16
(58) Field of Search ..................... 356/455; 250/559.16, 250/559.17, 559.18

(56) References Cited

U.S. PATENT DOCUMENTS

| | | | | |
|---|---|---|---|---|
| 3,938,662 A | * | 2/1976 | Ernst et al. ................... 209/554 |
| 4,540,887 A | * | 9/1985 | Minerd et al. ............. 250/559.4 |
| 4,547,896 A | * | 10/1985 | Ohtombe et al. ............ 382/135 |
| 5,139,339 A | * | 8/1992 | Courtney et al. ....... 250/559.16 |
| 5,640,244 A | * | 6/1997 | Hellstrom et al. ........... 356/446 |
| 6,122,042 A | * | 9/2000 | Wunderman et al. .......... 356/73 |
| 6,585,341 B1 | * | 7/2003 | Walker et al. ................. 347/14 |
| 6,600,167 B2 | * | 7/2003 | Sano ...................... 250/559.11 |
| 6,685,313 B2 | * | 2/2004 | Scofield et al. ......... 250/559.01 |
| 6,725,207 B2 | * | 4/2004 | Swimm ........................ 706/20 |
| 2001/0020688 A1 | * | 9/2001 | Kawamura et al. ....... 250/559.4 |
| 2003/0110963 A1 | * | 6/2003 | Martin et al. ................. 101/147 |

FOREIGN PATENT DOCUMENTS

EP 1136403 9/2001

* cited by examiner

Primary Examiner—Michael P. Stafira
Assistant Examiner—Juan D Valentin, II
(74) Attorney, Agent, or Firm—G.E. Ehrlich (1995) Ltd.

(57) ABSTRACT

Apparatus and method for discriminating between plate and interleave paper in a CTP device having a cassette with printing plates and interleave paper. The device uses a light source for illuminating the topmost object in the cassette, a first optical sensor for receiving direct light reflected from the topmost object, a second optical sensor for receiving dispersed light reflected from the topmost object, means for comparing light received by the second optical sensor with light received by the first optical sensor, and means for determining the topmost object type based on the comparison.

15 Claims, 5 Drawing Sheets

SURFACE REFLECTIVITY DISCRIMINATING DEVICE

This is a Continuation In Part of U.S. patent application Ser. No. 10/252,039 filed on Sep. 23, 2002.

FIELD OF THE INVENTION

The present invention relates to a discriminating device for discriminating between two kinds of objects based on surface reflectivity differences thereof, and more specifically to a device for discriminating between printing-plate and interleaf paper.

BACKGROUND OF THE INVENTION

In CTP devices for direct imaging on printing plates, the plates are accommodated in a magazine, or cassette and provided one by one to be exposed by the imaging device.

The plates provided in the cassette are usually separated by interleaf paper, interposed between the plates, to prevent friction damages to the plates' emulsion-covered surfaces.

In the course of imaging plates, the plate placed at the top of the stack is picked and transferred to the exposure area for imaging. If an interleaf paper (slip-sheet) is placed at the top of the stack, the paper is picked and disposed of.

Accordingly, discriminating means for discriminating between plate and paper are used, to correctly identify the topmost object on the stack.

Published application EP 1136403 describes a discriminating device comprising two optical sensors. One of the sensors reacts to light reflected by both plate and paper, while the second sensor reacts only to light reflected by a plate. The first and the second sensors are placed on the optical axis of the light reflected from the sensed surface. Both sensors react to a predetermined intensity of reflected light. The difference is that the second sensor is inclined and its predetermined intensity is lower, in order to react to polymer surface only.

The disadvantage of the method of EP 1136403 lies in its low discrimination factor ('paper' to 'metal' signal ratio), which would require intensity (threshold) adjustments per batch of plates of the same type having different reflectivity, on top of intensity adjustment per plate-type.

There is need for a discriminating device that overcomes the shortcomings of existing devices. The required device should be independent of variations in material and of sub-variations within plates of the same material.

SUMMARY OF THE INVENTION

The proposed surface discriminating method and device are free of the drawbacks of existing solutions, due to extended ratio of plate sensing to paper sensing signals, covering all differences between different materials and batches of the same material.

According to one aspect of the present invention, there is provided an apparatus for discriminating between objects having different surface reflectivity, said objects positioned in one of a plurality of angles relative to said apparatus, comprising:

a light source for illuminating an object;

a first optical sensor mounted relative to said light source, said first optical sensor receiving direct light reflected from said object in a first one of said plurality of angles;

a second optical sensor mounted relative to said light source, said second optical sensor receiving direct light reflected from said object in a second one of said plurality of angles;

a third optical sensor mounted relative to said light source, said third optical sensor receiving dispersed light reflected from said object in any of said plurality of angles;

adding means for computing the sum of a light signal received by said first sensor and a light signal received by said second sensor;

computation means for comparing a light signal received by said third optical sensor with said sum, said computation means connected with said adding means and with said third optical sensor; and means for determining said object type, said means for determining connected with said computation means.

In one embodiment, the computation means comprise means for subtracting.

The apparatus may additionally comprise a first amplifier connected with said adding means and a second amplifier connected with said third optical sensor, wherein said first amplifier and said second amplifier are connected with said computation means.

The means for determining may comprise a comparator and a reference, wherein said comparator compares an input thereof, received from said computation means, with said reference.

The apparatus may additionally comprise a third amplifier connected with said computation means and with said means for determining.

According to another aspect of the present invention, there is provided a CTP device for imaging printing plates stacked in a cassette, said plates separated by paper sheets, said cassette positioned in one of a plurality of angles, comprising:

an imaging system;

discriminating means for determining the type of a topmost object in said cassette, said discriminating means comprising:

a light source for illuminating said topmost object;

a first optical sensor mounted relative to said light source, said first optical sensor receiving direct light reflected from said topmost object in a first one of said plurality of angles;

a second optical sensor mounted relative to said light source, said second optical sensor receiving direct light reflected from said topmost object in a second one of said plurality of angles;

a third optical sensor mounted relative to said light source, said third optical sensor receiving dispersed light reflected from said topmost object in any of said plurality of angles;

adding means for computing the sum of a light signal received by said first sensor and a light signal received by said second sensor;

computation means for comparing a light signal received by said third optical sensor with said sum, said computation means connected with said adding means and with said third optical sensor; and means for determining said topmost object type, said means for determining connected with said computation means.

In one embodiment, the computation means comprise means for subtracting.

The apparatus may additionally comprise a first amplifier connected with said adding means and a second amplifier connected with said third optical sensor, wherein said first amplifier and said second amplifier are connected with said computation means.

The means for determining may comprise a comparator and a reference, wherein said comparator compares an input thereof, received from said computation means, with said reference.

The apparatus may additionally comprise a third amplifier connected with said computation means and with said means for determining.

In one embodiment, the comparator's output is a logic high when said topmost object is a plate and a logic low when said topmost object is a paper sheet.

In another embodiment, the comparator's output is a logic low when said topmost object is a plate and a logic high when said topmost object is a paper sheet.

In yet another aspect of the present invention, there is provided a method of discriminating between objects having different surface reflectivity, said objects positioned in one of a plurality of angles, comprising the steps of:

providing a light source for illuminating an object;

providing a first optical sensor mounted relative to said light source, said first optical sensor receiving direct light reflected from said object in a first one of said plurality of angles;

providing a second optical sensor mounted relative to said light source, said second optical sensor receiving direct light reflected from said object in a second one of said plurality of angles;

providing a third optical sensor mounted relative to said light source, said third optical sensor receiving dispersed light reflected from said object in any one of said plurality of angles;

comparing a light signal received by said third optical sensor with a sum of the light signals received by said first and second optical sensors; and determining said object type based on said step of comparing.

In one embodiment, the step of comparing comprises subtracting.

In yet another aspect of the present invention, there is provided, in a CTP machine, a method of determining the type of a topmost object in a plate loading cassette, said cassette positioned in one of a plurality of angles, comprising the steps of:

providing a light source for illuminating said topmost object;

providing a first optical sensor mounted relative to said light source, said first optical sensor receiving direct light reflected from said topmost object in a first one of said plurality of angles;

providing a second optical sensor mounted relative to said light source, said second optical sensor receiving direct light reflected from said topmost object in a second one of said plurality of angles;

providing a third optical sensor mounted relative to said light source, said third optical sensor receiving dispersed light reflected from said topmost object in any one of said plurality of angles;

comparing a light signal received by said third optical sensor with a sum of the light signal received by said first and second optical sensors; and determining said topmost object type based on said step of comparing.

In one embodiment, the step of comparing comprises subtracting.

BRIEF DESCRIPTION OF THE DRAWINGS

For a better understanding of the invention and to show how the same may be carried into effect, reference will now be made, purely by way of example, to the accompanying drawings, in which similar objects are referenced by similar numerals.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PRESENT INVENTION

Figure 1:
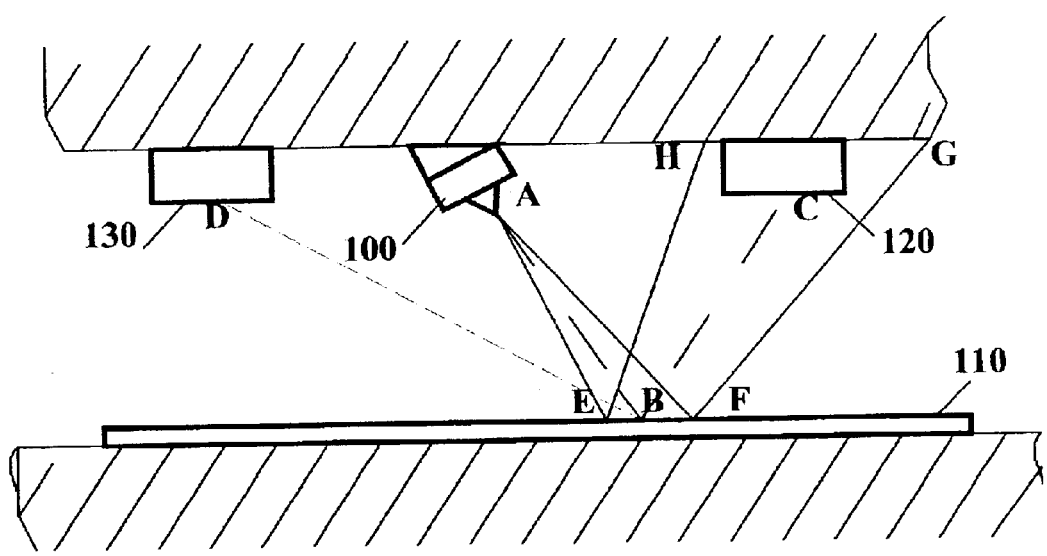
FIG. 1 is a schematic representation of a discriminating device according to a first embodiment of the present invention.

FIG. 1 is a schematic representation of a discriminating device according to the present invention, consisting of light source 100, for example light emitting diode (LED) such as SFH-484, available from Siemens of Munich, Germany, two optical sensors 120 and 130, such as SFH-235, also available from Siemens of Munich, Germany and an object 110 to be detected, having a reflective surface.

Figure 2:
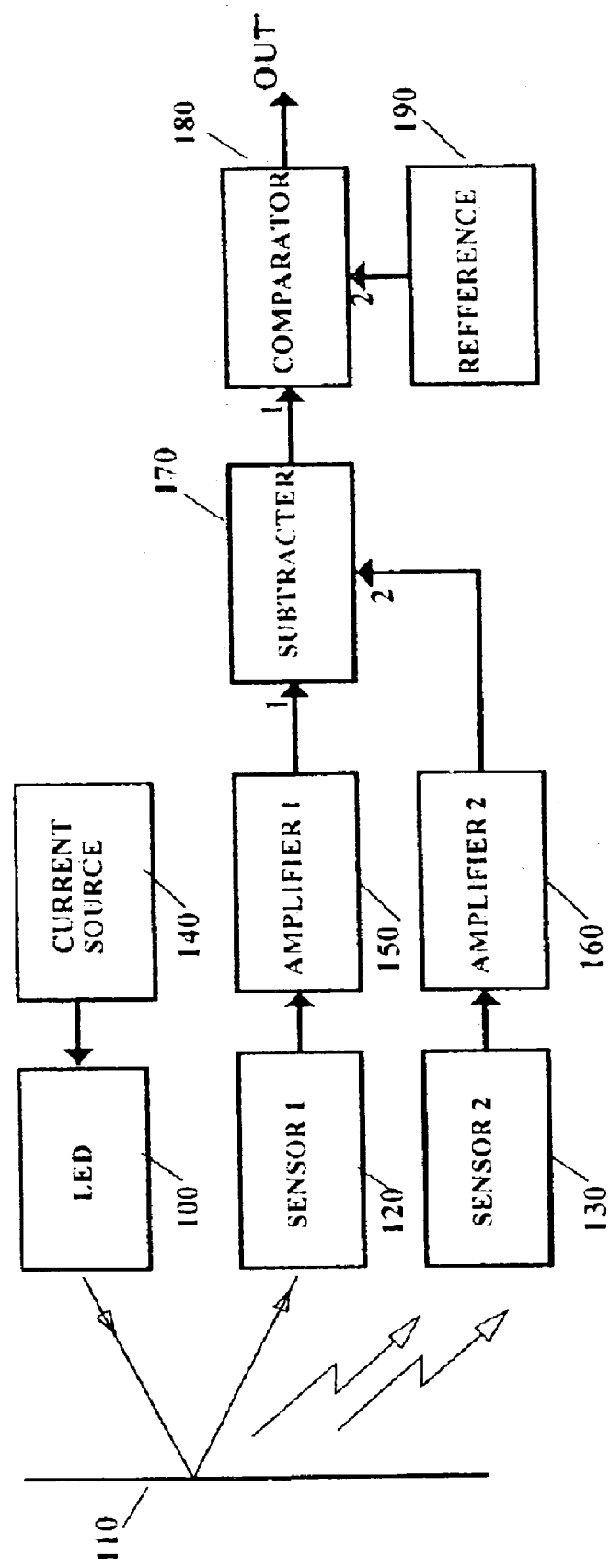
FIG. 2 is a functional scheme of a discriminating device according to the present invention.

FIG. 2 is a more detailed functional scheme of a discriminating device according to the present invention. Light source 100 is energized by current source 140. A first sensor 120 is mounted so as to receive the direct reflection of the LED beam. Sensor 120 is connected through a first amplifier 150 to the input 1 of subtracter 170. The second sensor 130 is mounted outside of the optical axis of the reflective light, at some distance from sensor 120, preferably 2–4 cm, in order to detect the dispersed portion of the reflected light. Sensor 130 is connected through a second amplifier 160 to the input 2 of subtracter 170. The output of subtracter 170 is connected to the first input of comparator 180. The second input of the comparator 180 is connected to reference 190. In another preferred embodiment, an additional amplifier may be placed between subtracter 170 and comparator 180, to adjust the subtracter 170 output to the comparator 180 input. In yet another preferred embodiment of the present invention, subtracter 170 may be substituted with a divider or a multiplier (not shown).

Figure 3:
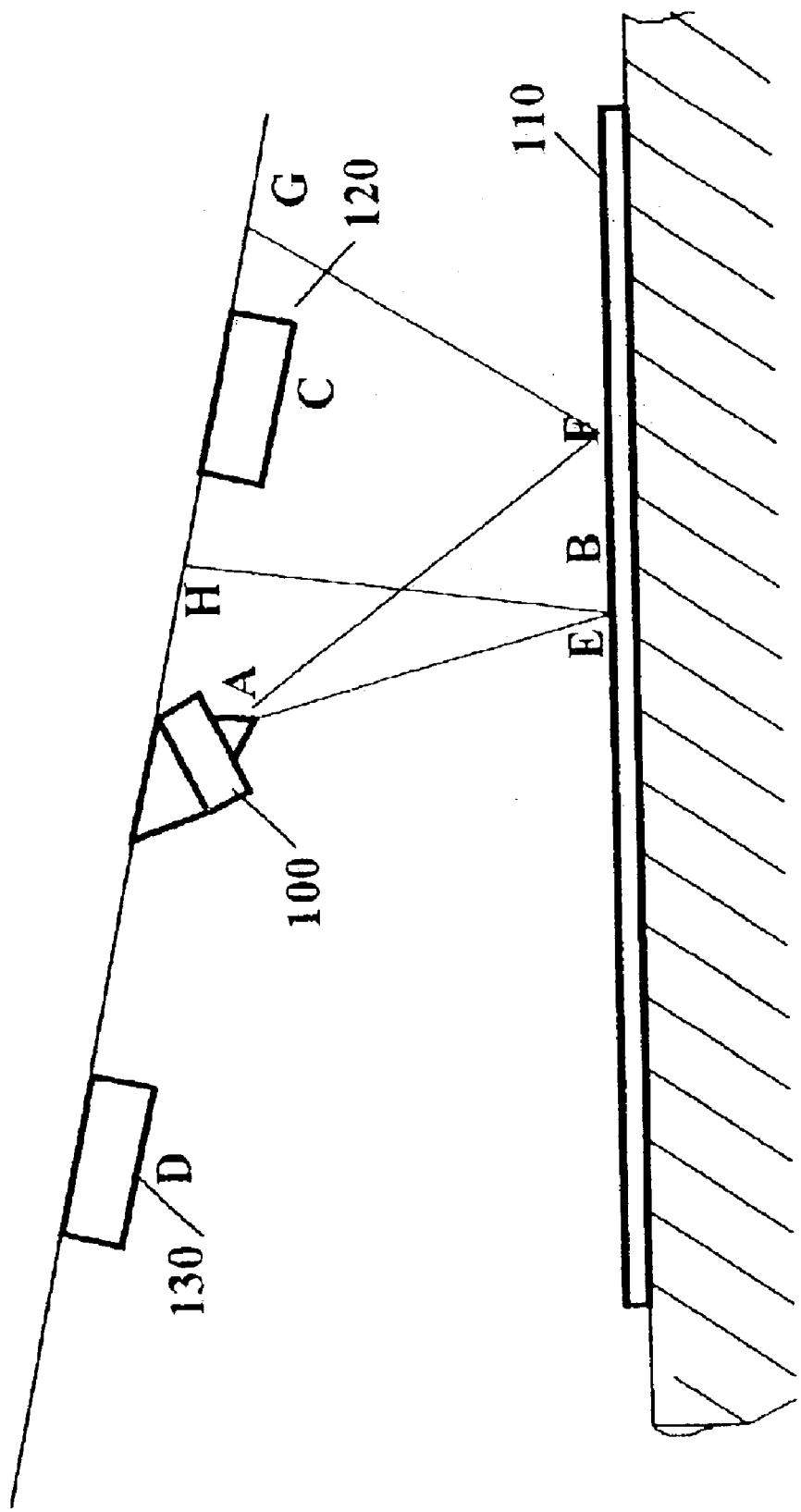
FIG. 3 is a schematic representation of a discriminating device according to a second embodiment of the present invention.

Referring back to FIG. 1, the distance between the sensors 120 and 130 is determined based on the following considerations: Sensor 120, intended to detect the directly reflected portion of the light, should be placed on the optical path of the directly reflected beam BC. The shorter the optical path ABC, the stronger will be the signal to noise ratio, which is desirable. Sensor 130, intended to detect the dispersed portion of the light, should be placed outside the area AEFGH of direct light reflection. It can be mounted, for example, on the other side of the light source 100, as shown in FIGS. 1 and 3, or on the same side, as shown in FIG. 2. The tradeoff in the placement considerations of sensor 130 is between decreasing the optical distance DB, from the sensor 130 to the direct beam reflecting point, which helps to increase the signal to noise ratio, and keeping the sensor 130 far enough from the light source so as not to fall within the direct light reflection area AEFGH and to be far enough from the investigated surface so that a big enough dispersed portion of light reaches it.

FIG. 3 is a schematic representation of another embodiment of the discriminating device of the present invention. The only difference between the embodiments of FIG. 1 and FIG. 3 is in the layout of the light source 100 and the sensors 120 and 130. In the embodiment of FIG. 3 those elements are laid out on a sloped surface, so that the vertical distance of sensor 120 from the detected surface is smaller comparing to that shown in FIG. 1, so the sensor signal will be stronger. On the other hand, the vertical distance of sensor 130 from the detected surface is big enough to receive enough dispersed light.

The device operates as follows:

After power up, constant current from the current source 140 causes the lighting of LED 100. This light falls onto detected surface 110. If the detected surface 110 is smooth, like a plate, then the directly reflected portion Ds of the light will be big and the dispersed portion Ss will be small. If the detected surface is rough, like paper, then the directly reflected portion Dr of the light will be smaller than Ds and the dispersed portion Sr will be bigger than Ss.

The first and second sensors' signals are amplified by first amplifier 150 and second amplifier 160, respectively.

The output signal of the second amplifier 160 is subtracted from the output signal of the first amplifier 150 in subtracter 170. When a plate is detected, the result of the subtraction (Ds−Ss) yields a high value (because, as mentioned above, a low signal is subtracted from a high signal). When paper is detected, the result of the subtraction (Dr−Sr) yields a low value (because, as mentioned above, a high signal is subtracted from low signal).

In other words, when detecting plate, the result of the subtraction yields a high level signal and, when detecting paper, the result of the subtraction yields a low level signal. Comparator 180 compares the subtraction result with medium level reference 190. If the detected surface is a plate, then the comparison will result with a logic high and if the detected surface is paper, then the comparison will result with a logic low, or vice versa if reverse logic is used.

In a preferred embodiment of the present invention, the amplifiers 150 and 160 have different amplification coefficients, chosen so as to maximize the difference between subtracter 170 outputs for plate and paper, thus increasing the discrimination factor.

Let Vsns1 and Vsns2 be the outputs voltage of direct (120) and dispersed (130) light sensors respectively.

Let A1 and A2 be the amplification factors of first (150) and second (160) amplifiers respectively.

Let U1 and U2 be the output voltage of first (150) and second (160) amplifiers respectively, where:

$$U1 = A1 * Vsns1$$

$$U2 = A2 * Vsns2$$

When a plate is sensed:

$$U1(pl) = A1 * Vsns1(pl)$$

$$U2(pl) = A2 * Vsns2(pl)$$

The output of subtracter 170 will be:

$$IND(pl) = U1(pl) - U2(pl)$$

When paper is sensed:

$$U1(pa) = A1 * Vsns1(pa)$$

$$U2(pa) = A2 * Vsns2(pa)$$

The output of subtracter 170 will be:

$$IND(pa) = U1(pa) - U2(pa)$$

A1 and A2 will preferably be chosen so as to maximize the ratio IND(pl):IND(pa).

Figure 4:
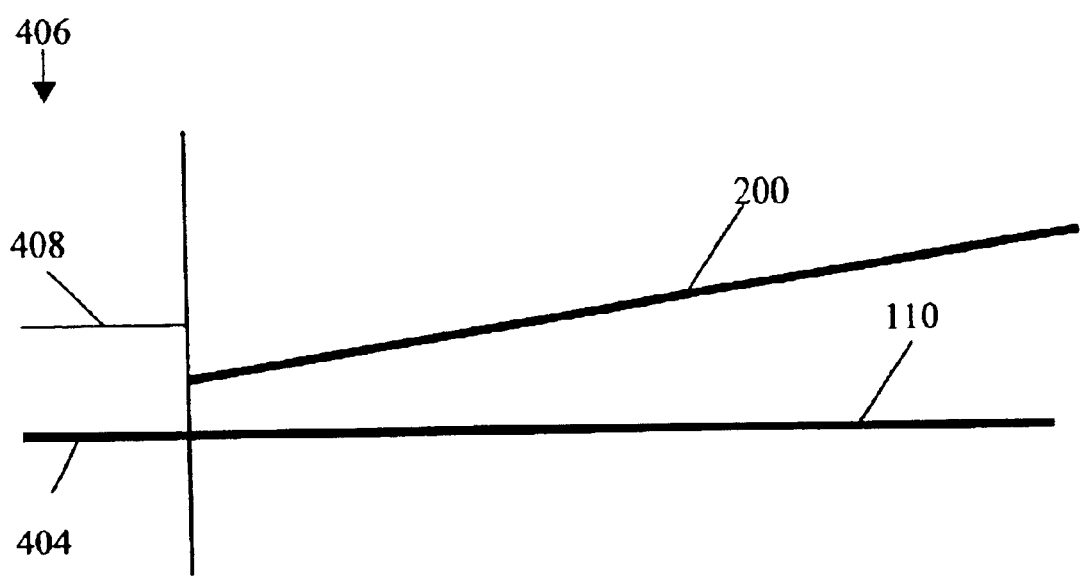
FIG. 4 is a schematic representation of a dual-cassette configuration loading system.

FIG. 4 is a schematic representation of a dual-cassette plate loader, as used for example in conjunction with Lotem 800, produced by Creo Inc., Canada. The dual cassette configuration comprises two cassettes, preferably mounted on a removable trolley (not shown). The two cassettes preferably contain plates of different sizes and are positioned such that one cassette 110 is horizontal and the other cassette 200 is inclined. Only one of the cassettes 110 and 200 is in a loading position at any given moment. In FIG. 4, cassette 110 is positioned at the loading position, such that its front part 404 resides inside the imaging compartment 406 of the CTP machine. Beam 408, also residing in the imaging compartment 406, preferably holds the discriminating device of the present invention (not shown). When a change of cassette is required, the current cassette is retracted (manually or automatically and the second cassette is positioned with its front side inside the imaging compartment.

Figure 5:
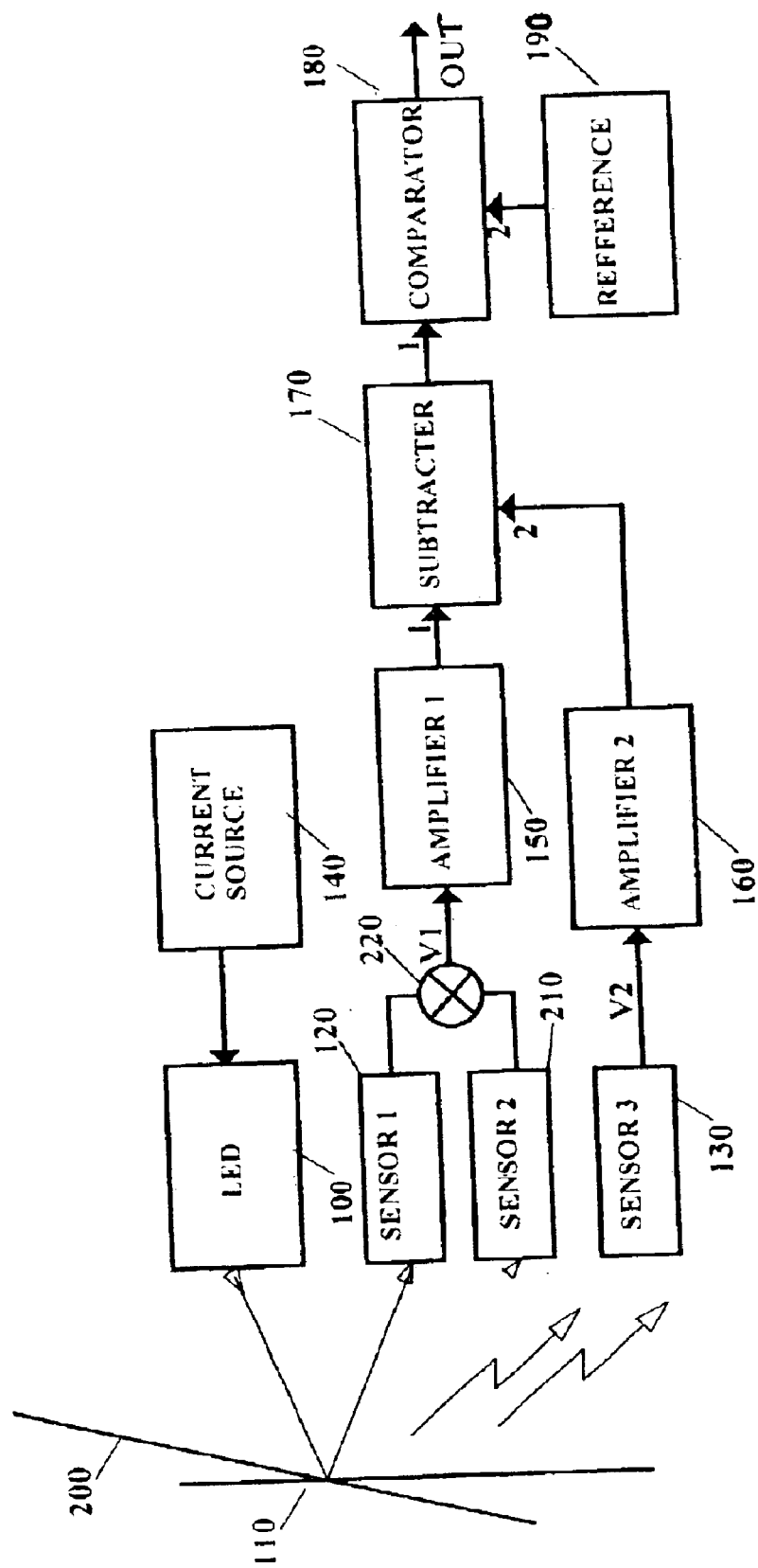
FIG. 5 is a schematic representation of a discriminating device for use with the configuration of FIG. 4.

FIG. 5 is a schematic representation of a discriminating device according to another embodiment of the present invention, designed to provide paper-plate discrimination for the dual-cassette configuration, having to deal with either horizontal or inclined surfaces. The discriminating device comprises light source 100, for example light emitting diode (LED) such as SFH484, available from Siemens of Munich, Germany, three optical sensors 120, 130 and 210, such as SFH-235, also available from Siemens, a first object 110 to be detected, having a reflective surface, and a second object 200 to be detected. Object 110 is positioned horizontally with respect to the discriminating device and object 200 is positioned at an angle. The device of FIG. 5 additionally comprises an adder 220, designed to add the signals of sensors 120 and 210, amplifiers 150 and 160, subtracter 170, comparator 180 and reference 190.

The operation of the device of FIG. 5 is similar to that described in conjunction with FIG. 2. When a horizontal object, such as plate 110, is positioned at the detection position, the light directly reflected from the object will be sensed by sensor 120 and will not be sensed by sensor 210. Consequently, the sum produced by adder 220 will approximately equal the signal of sensor 120. In this case the device operates the same way as the device of FIG. 2. When a tilted object, such as plate 200, is positioned at the detection position, the light directly reflected from the object will be sensed by sensor 210 and will not be sensed by sensor 120. Consequently, the sum produced by adder 220 will approximately equal the signal of sensor 210. Again the operation of the discriminating device will be similar to that of the device of FIG. 2.

It will be appreciated that although the embodiments of the present invention were described in conjunction with a plate loading system for CTP, the present invention lends itself to any discriminating device for discriminating between two kinds of objects based on surface reflectivity differences thereof.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description. For example, the system of the present invention is not limited to two different angles of objects. Rather, any number of objects to be discriminated, positioned at different angles to the discriminating device, may be discriminated by the system of the present invention, by using additional optical sensors in a similar manner to what was described hereinabove.

What is claimed is:

1. Apparatus for discriminating between objects having different surface reflectivity, said objects positioned in one of a plurality of angles relative to said apparatus, comprising:

a light source for illuminating an object;

a first optical sensor mounted relative to said light source, said first optical sensor receiving direct light reflected from said object in a first one of said plurality of angles;

a second optical sensor mounted relative to said light source, said second optical sensor receiving direct light reflected from said object in a second one of said plurality of angles;

a third optical sensor mounted relative to said light source, said third optical sensor receiving dispersed light reflected from said object in any of said plurality of angles;

adding means for computing the sum of a light signal received by said first sensor and a light signal received by said second sensor;

computation means for comparing a light signal received by said third optical sensor with said sum, said computation means connected with said adding means and with said third optical sensor; and means for determining said object type, said means for determining connected with said computation means.

2. The apparatus of claim 1, wherein said computation means comprises means for subtracting.

3. The apparatus of claim 1, additionally comprising a first amplifier connected with said adding means and a second amplifier connected with said third optical sensor, wherein said first amplifier and said second amplifier are connected with said computation means.

4. The apparatus of claim 1, wherein said means for determining comprises a comparator; and additionally comprising a reference, wherein said comparator compares an input thereof, received from said computation means, with said reference.

5. The apparatus of claim 3, additionally comprising a third amplifier connected with said computation means and with said means for determining.

6. A CTP device for imaging printing plates stacked in a cassette, said plates separated by paper sheets, said cassette positioned in one of a plurality of angles, comprising:

an imaging system;

discriminating means for determining the type of a topmost object in said cassette, said discriminating means comprising:

a light source for illuminating said topmost object;

a first optical sensor mounted relative to said light source, said first optical sensor receiving direct light reflected from said topmost object in a first one of said plurality of angles;

a second optical sensor mounted relative to said light source, said second optical sensor receiving direct light reflected from said topmost object in a second one of said plurality of angles;

a third optical sensor mounted relative to said light source, said third optical sensor receiving dispersed light reflected from said topmost object in any of said plurality of angles;

adding means for computing the sum of a light signal received by said first sensor and a light signal received by said second sensor;

computation means for comparing a light signal received by said third optical sensor with said sum, said computation means connected with said adding means and with said third optical sensor; and means for determining said topmost object type, said means for determining connected with said computation means.

7. The apparatus of claim 6, wherein said computation means comprises means for subtracting.

8. The apparatus of claim 6, additionally comprising a first amplifier connected with said adding means and a second amplifier connected with said third optical sensor, wherein said first amplifier and said second amplifier are connected with said computation means.

9. The apparatus of claim 6, wherein said means for determining comprises a comparator; and additionally comprising a reference, wherein said comparator compares an input thereof, received from said computation means, with said reference.

10. The apparatus of claim 9, wherein said comparator's output is a logic high when said topmost object is a plate and a logic low when said topmost object is a paper sheet.

11. The apparatus of claim 9, wherein said comparator's output is a logic low when said topmost object is a plate and a logic high when said topmost object is a paper sheet.

12. A method of discriminating between objects having different surface reflectivity, said objects positioned in one of a plurality of angles, comprising the steps of:

providing a light source for illuminating an object;

providing a first optical sensor mounted relative to said light source, said first optical sensor receiving direct light reflected from said object in a first one of said plurality of angles;

providing a second optical sensor mounted relative to said light source, said second optical sensor receiving direct light reflected from said object in a second one of said plurality of angles;

providing a third optical sensor mounted relative to said light source, said third optical sensor receiving dispersed light reflected from said object in any one of said plurality of angles;

comparing a light signal received by said third optical sensor with a sum of the light signals received by said first and second optical sensors; and determining said object type based on said step of comparing.

13. The method of claim 12, wherein said step of comparing comprises subtracting.

14. In a CTP device, a method of determining the type of a topmost object in a plate loading cassette, said cassette positioned in one of a plurality of angles, comprising the steps of:

provisioning a light source for illuminating said topmost object;

providing a first optical sensor mounted relative to said light source, said first optical sensor receiving direct light reflected from said topmost object in a first one of said plurality of angles;

providing a second optical sensor mounted relative to said light source, said second optical sensor receiving direct light reflected from said topmost object in a second one of said plurality of angles;

providing a third optical sensor mounted relative to said light source, said third optical sensor receiving dispersed light reflected from said topmost object in any one of said plurality of angles;

comparing a light signal received by said third optical sensor with a sum of the light signal received by said first and second optical sensors; and determining said topmost object type based on said step of comparing.

15. The method of claim 14, wherein said step of comparing comprises subtracting.

* * * * *